(12) United States Patent
Lin-Hendel

(10) Patent No.: US 7,167,752 B2  
(45) Date of Patent: Jan. 23, 2007

(54) ELECTRONIC ELECTRICAL AND ELECTRO-MAGNETIC HEALTH ENHANCEMENT AND STIMULATION DEVICE

(76) Inventor: Catherine Lin-Hendel, 26 Ridge Rd., Summit, NJ (US) 07901

( * ) Notice: Subject to any disclaimer, the term of this patent is extended or adjusted under 35 U.S.C. 154(b) by 580 days.

(21) Appl. No.: 10/439,163

(22) Filed: May 15, 2003

(65) Prior Publication Data  
US 2004/0230256 A1 Nov. 18, 2004

(51) Int. Cl.  
A61N 1/00 (2006.01)  
A61H 39/02 (2006.01)  
A61M 21/00 (2006.01)  
A61B 17/00 (2006.01)  
A61B 19/00 (2006.01)

(52) U.S. Cl. .............................. 607/46; 607/2; 607/74; 607/59; 607/68; 607/69; 607/70; 600/548; 600/26; 606/204; 128/898; 128/907

(58) Field of Classification Search ............ 607/2, 607/46, 74, 59, 68–70; 600/548, 26; 606/204; 128/898, 907  
See application file for complete search history.

(56) References Cited

U.S. PATENT DOCUMENTS

| | | | | |
|---|---|---|---|---|
| 4,765,310 A | * | 8/1988 | Deagle et al. | 600/14 |
| 5,195,517 A | * | 3/1993 | Chen | 607/3 |
| 5,397,338 A | * | 3/1995 | Grey et al. | 607/115 |
| 6,421,560 B1 | * | 7/2002 | Yoo | 600/548 |

* cited by examiner

Primary Examiner—Robert E. Pezzuto  
Assistant Examiner—Natasha Patel  
(74) Attorney, Agent, or Firm—Jean-Marc Zimmerman, Esq.

(57) ABSTRACT

An electronic acupressure aide and stimulating device implemented using a hand-held or palm-held electronic computing device or another computing device which may be a designated unit. The electronic acupressure aide and stimulating device allows a practitioner to apply a pulse sequence to a set of predetermined acu-points such as those related to acupressure, acupuncture, trigger points or Jin-Shin Jyutsu, to name a few. A displayed chart related to the acu-points identifies the health condition and the pulse sequence.

24 Claims, 15 Drawing Sheets

The Bladder Meridian of Foot Taiyang

The Kidney Meridian of Foot Shaoyin

The Gallbladder Meridian of Foot Shaoyang

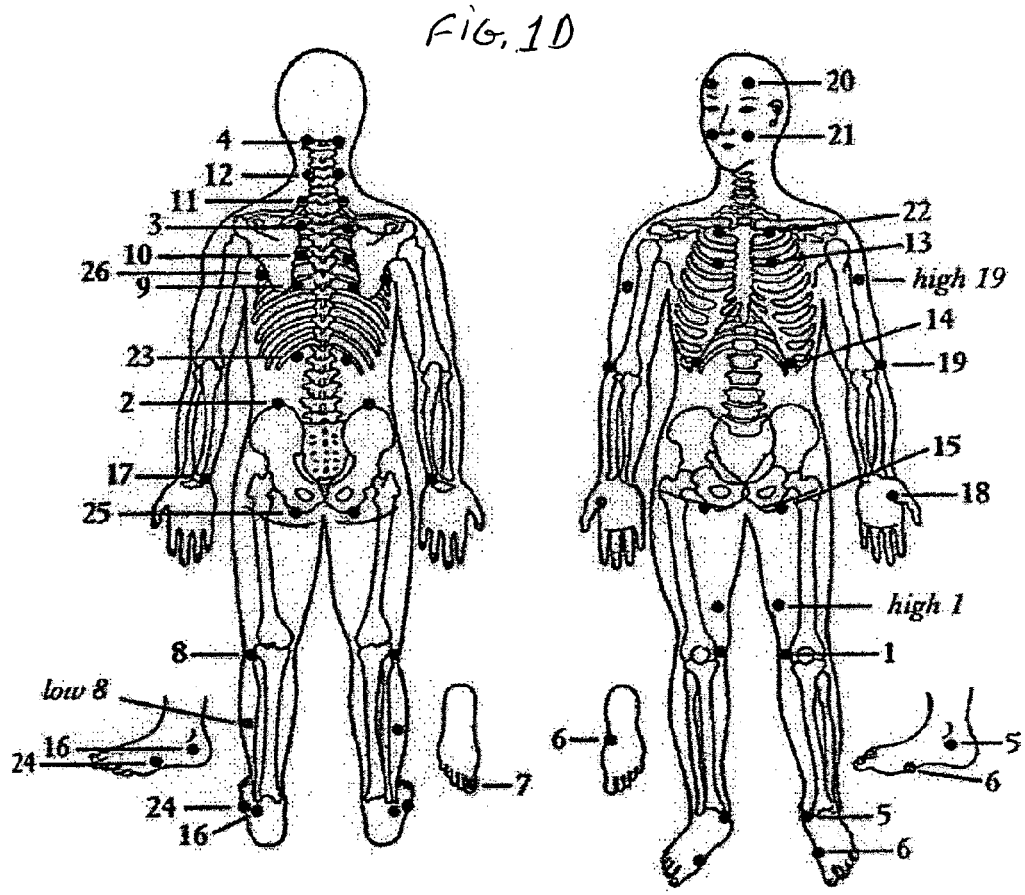

Index of Safety Energy Locks (SEL)

| To Help | Use SEL | To Help | Use SEL | To Help | Use SEL |
|---|---|---|---|---|---|
| Abdomen | 1, 15, 23 | Ear | 5, 20 | Muscles | 8, 16 |
| Ankle | 9, 15, 17 | Elimination | 8, 16 | Neck | 11, 12, 13, 16 |
| Appetite | 13 | Emotional equilibrium | 12, 22, 23, 24 | | |
| Arm | 9, 11, 12 | | | Nervous system | 17 |
| Back | 2, 6, 9, 19 | Equilibrium | 6, 20 | | |
| Bloat | 1, 15, 17 | Eye | 4, 20 | Pelvis | 3, 8 |
| Brain | 23 | Fever | 3 | Reproductive system | 8, 13, 16, 17 |
| Breast | 17, 19 | Foot | 9, 15 | | |
| Breathing | 1, 2, 3 | Head | 1, 7, 16, 18 | Shakiness | 24, 26 |
| Chest | 6, 9, 10, 13 | Heart | 10, 15, 17 | Shoulder | 10, 11, 13 |
| Circulation | 10, 23 | Hip | 6, 9, 11, 14 | Throat | 3, 4, 10 |
| Colds | 3 | Insomnia | 4, 18 | Thyroid | 14 |
| Convulsions | 7 | Knee | 10, 15 | Weight | 21 |
| Digestion | 2, 5, 7, 19 | Leg | 2, 9, 11, 15 | Wrist | 9, 11 |
| Dizziness | 21 | Mental clarity | 7, 20, 21, 25 | | |

Figure 2

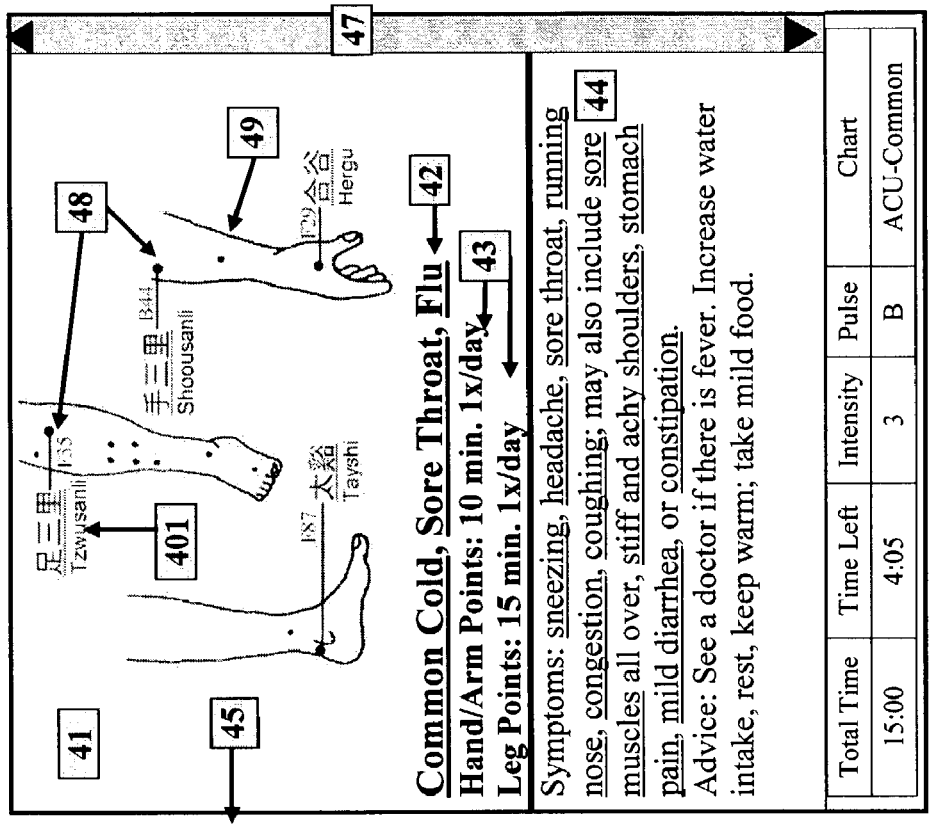
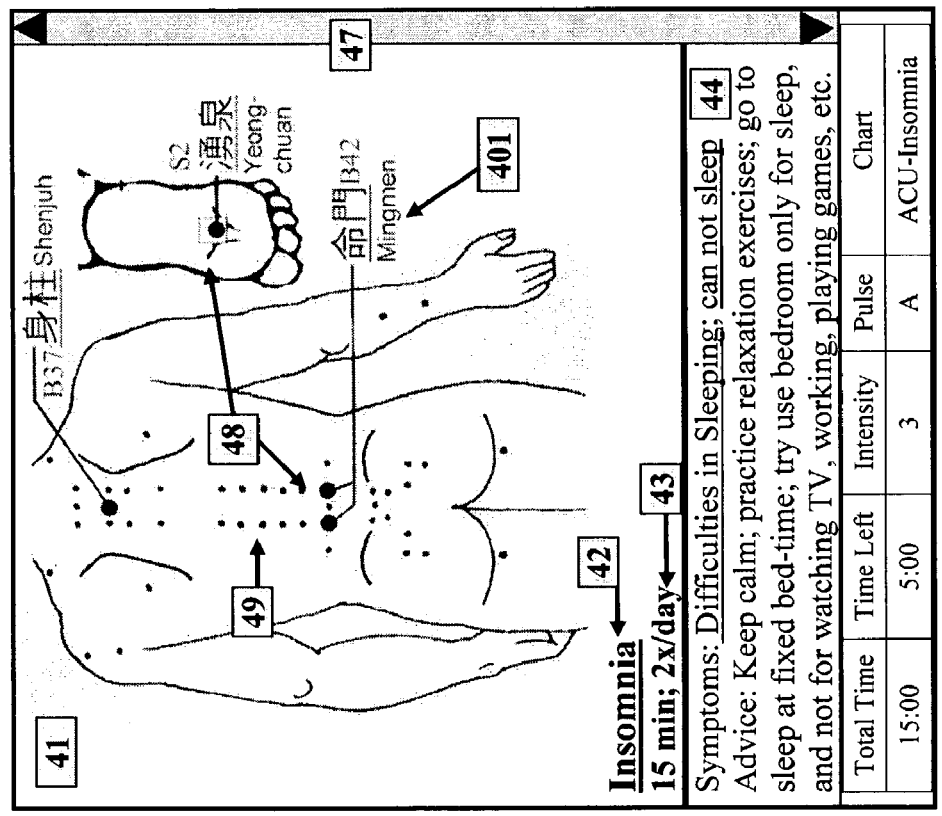
Figure 4A

ELECTRONIC ELECTRICAL AND ELECTRO-MAGNETIC HEALTH ENHANCEMENT AND STIMULATION DEVICE

FIELD OF THE INVENTION

The present invention is related to the field of medial and health enhancement devices and therapies, and more specifically, to a compact electronic multi-purpose electrical/ eletro-magnetic stimulating device.

BACKGROUND OF THE INVENTION

The ancient, traditional, and present eastern health and medical practices all evolve around the concept and theory of an invisible life-energy that permeates the environment, and circulates in the human body via a system of channels and gateways. This life-energy is believed to nourish and power all living things. This invisible life-energy is called "qi" or "chi" (氣 in China and Japan, and Prana in India. Eastern medical treatments all involve delivering and improving the flow of this life-energy to the ill, either biochemically converting from herbal remedies, deriving from the environment, or delivering via a healer to the patient's system of life-energy flow channels. One such example is Acupuncture, which use acupuncture needles punctured through a patient's skin to gateways to his/her life-energy channels to derive energy from the environment to unblock the patient's blockage in his life-energy flow.

Traditional Chinese Health/Medical Theories and Acupuncture:

The Traditional Chinese Medical Art of Acupuncture is widely practiced all over the world, for enhancing health and treating illnesses. The practitioner inserts small gauge needles through skin, ranging from approximately 2 mm to 2.5 cm deep, into specific sets of "Points" in a system of Meridians and Collaterals, and Organ and Muscle Regions. According to the theories of the Traditional Chinese Medicine, Meridians and Collaterals ("Jinglou," 經絡) are channels where, life-energy ("qi" 氣 and blood ("shu" 血), or, rather, the micronutrients in the blood circulate, and the exchange of nutrient and bio-wastes takes place. The Meridians are the main channels, and the Collaterals are the branch channels. This system of Meridians and Collaterals include 12 regular Meridians, 8 extra Meridians, 15 Collaterals, 12 divergent Meridians, 12 Muscle Regions, and 12 Cutaneous Regions. Three of the 32 Meridians are illustrated in FIG. 1A. The "Points" where the Acupuncture needles are inserted into, are the specific sites located in the superficial cutaneous layer generally beneath the surface skin, and above the muscle regions, through which (the "Points"), the "qi"—of the organs ("Zang-Fu" 臟腑 muscles, nerves, and Meridians and Collaterals, is gated to the body surface. External energy can thus be gated into the Meridians, Collaterals, Zang-Fu, Muscles, and Nerves to help open blocked "qi" flow, and to amend inadequate "qi."

While Acupuncture is only one modality in the many different treatment modalities and methods in the Traditional Chinese Medicine, and these gateway "Points," have many uses and ramifications beyond Acupuncture, they are referred as Acu-Points in the Western nomenclature, due to the popularity of Acupuncture in the West. FIGS. 1B and 1C illustrate locations and names of some major Acu-Points. FIG. 1D lists 12 of the 27 Acu-Points on the Kidney Meridian of Foot Shaoyin, a Meridian shown in FIG. 1A. This list is taken from the text of "Chinese Acupuncture and Moxibustion," which was compiled by the International Acupuncture Training Centers and Acupuncture Institute of China, Academy of Traditional Chinese Medicine, on commission of the Ministry of Public Health. The name, location, indications (problems that can be treated by treating the Point), method, and the nearby blood vessels and nerves are described. Except for Point K1,the locations and methods are truncated in FIG. 1D for economy of space. In all of the texts of Traditional Chinese Medicine, the Acu-Points are organized/listed under the Meridian/Collateral and/or Muscle Regions each Point belong, along with the indications for each Point. The traditional Chinese medicine theorizes that ill health is due to blockage, imbalance, and inadequacy of the "qi," thus impediment to nutrient flow and blood circulation in certain areas of the body. Through these surface gateway Acu-Points, the "qi" and nutrient flow in the area of the ailed can be adjusted and re-balanced, to restore proper functioning. The imbalance or blockage of the "qi" and nutrient flow in certain pathways and regions of the body results in a certain set of Inter-correlated health conditions. Acupuncture treats these health conditions by inserting small gauge needles to a set of Acu-Points gated to the certain areas of certain Meridians and Collaterals that are related to these specific health conditions to eliminate blockage and achieve adequacy and balance in the "qi" and nutrient flow and circulation. Practitioners often rub and turn the needle between the thumb and the index finger holding the needle while inserting it into an Acu-Point. Such rubbing and turning action is said to produce a small amount of electrical energy that would be conducted through the needle to the Acu-Point to "kick-start" the stagnant energy—"qi" to flow. Acupuncture is proven effective in treating a very large array of chronic health conditions, pain, and aches, as well as enhancing physical and mental health and vitality. However, the Meridian and Collateral system is very complex, and mastery of the vast quantity, depth of knowledge of the subtlety and intricacy of the Meridian and Collateral system is required for the practice. The acupuncture needles are very fine, requiring accurate location and depth insertion to produce effective results, and to not accidentally miss-insert into a nerve, a blood vessel, or a wrong Point, causing pain, bleeding, and/or undesirable results. These risk aspects of the needle insertion of Acupuncture make the practice difficult to master, and patients reluctant to visit an acupuncturist.

Acupressure:

Acupressure is also a widely practiced traditional Chinese healing/therapeutic modality, literally called Finger Pressure in Chinese. This modality uses fingers to apply pressure to, and/or massage the Acu-Points to heal ailments or to enhance health, largely using the same "indications" as in Acupuncture. This technique has also become popular outside of Chinese communities. However, the difficulties of mastering the intricacy of the Meridian and Collateral system, and the risk of serious negative consequences resulting from applying strong pressure on a wrong Point are also significant problems in the Acupressure therapy.

Jin Shin Jyutsu:

Jin Shin Jyutzu was an obscure branch of the "qi" and Meridian based Traditional Chinese Medicine. It was revived and promoted by a Japanese man during early 1900's. The treatment art uses only the simple "touch" and "holding" with hands, on primarily 26 pairs of "safety-energy-locks" (SEL) located along five major Meridians, to remove blockages and stagnations of the life-energy flow, which, the practitioners of Jin-Shin Jyutsu believe to cause a variety of biological and mental disharmony and illnesses. By holding patient's five fingers of the hands, and the center of the palms, as well as the 26 pairs of energy-locks, the practitioners of the art believe, that the various "depths" and "flows" of the life-energy would be increased, improved, and balanced to achieve general well-being, and heal illnesses. This art was brought to the U.S. in the early 1960's, and promoted and practiced with excellent results. The 26 pairs of "safety energy-locks" in Jin Shin Jyutsu are actually a subset of key Acu-Points. The fingers, fingertips and palm centers are converging, connection, and crossover places and points of many Meridians. Jin Shin Jyutsu advocates that human hands are conduit of the healing energy that permeates in the environment as well as resides within the patient and the healer, and thus there is no need for the application of force/pressure in Jin Shin Jyutsu as is in Acupressure. The treatment is nevertheless time consuming, and at times awkward and tiring for the practitioner. Only two locations can be "touched"/"held" at the same time by one practitioner. Holding one pair of "safety-energy-locks" can take as much as tens of minutes to achieve noticeable effect—specified in Jin Shin Jyutsu as a pulsation under the touch, while many pairs of "safety energy-locks" often need to be treated for a particular health condition. FIG. 2 shows the 26 pairs of "safety energy locks," and a list of treatment subjects/areas with the corresponding SELs to be used for treating the subject/area.

Trigger Point Massage Therapy:

Trigger Point Massage Therapy theorizes that when muscles are tight, over used, under used, improperly used, or injured, lactic acid and metabolic and inflammation waste products accumulate in concentration at specific locations on the muscles. These locations are called Trigger Points, examples of which are shown in FIG. 3. The waste accumulation at a Trigger Point impedes blood circulation, tighten muscles, and affects an entire region of muscle, tendon, and ligament tissues around the Trigger Point, manifesting in increasing soreness and pain, and results in the build-up of calcification and scar tissues in the area if not properly treated. The Trigger Points that have accumulated excessive lactic acid and other waste products produce an aching, sore sensation when pressed. The Trigger Point Massage is based on the premise that when adequate pressure is applied through surface skin over a sore Trigger Point, the force momentarily presses blood and fluid out of the Trigger Point. The release of the pressure creates a "starving vacuum," causing blood and fluids from the surrounding area to "rush" to the Trigger Point, thus flushing out the accumulated waste product and toxin. Continual treatment would break up the calcification and scar tissue that were formed over-time in the tissues in the affected area, and restore proper circulation and health to the muscle/tendon/ligament tissues in the area. A Trigger-Point massage therapist uses a finger, a knuckle, or an elbow to apply considerable force/pressure on the aching sore Trigger Points, which are located deep in the muscle tissue. The considerable force required, as well as the separate and depth locations of the Trigger Points, make the treatment process laborious and slow—by applying pressure with a thumb or elbow, one-point-at-a-time. This time and energy consuming shortcoming exists also in the Acupressure therapy.

Electronic Muscle Stimulation (EMS) and Transcutaneous Electronic Nerve Stimulation (TENS):

In orthopedic physical therapies chiropractic therapies dealing with injured, aching, and tense muscles, electrical pulses can be applied via conductive gel-pads on skin areas over two ends of an affected muscles and/or associated nerves, to involuntarily contract (pulse-on) and relax (pulse-off) muscles, and to stimulate nerves to reduce pain, promote healing, and restore function. These treatments are called Electronic Muscle Stimulation (EMS) and Transcutaneous Electronic Nerve Stimulation (TENS). The conventional electronic pulse generation devices used for such physical/chiropractic therapies generate a train of electronic pulses with constant frequency, amplitude, and wave shape, which are chosen and set from a range of available options or a set of "dials" by the practitioner for the patient. Biological subjects, such as nerves, muscles, ligaments, and tendons tend to get "trained to" (become "use to") an unchanging stimulus over time, and gradually come to ignore such unchanging stimulus, and cease to respond.

SUMMARY OF THE INVENTION

The inventor of the present invention surmised, postulated, and proved the following: (1) that the "life energy" is a form of electro-magnetic energy, manifests in the form of a slight electrical current and/or a slight magnetic field, (2) the acupuncture needles served as antenna that collect electromagnetic wave/energy in the environment, and inject the energy into the Acu-Points where the needles are inserted.

The present invention contemplates generating and delivering electrical and/or electromagnetic energy via conductive gel-pads with embedded electrically conductive material or conductive coils, to stimulate, improve, and promote life-energy flow, blood flow, and nerve, organ, muscle functions, and proper bone growth and healing. The present invention replaces the following: (1) the use of needles as practiced in Acupuncture, (2) the application of considerable pressure via thumbs, knuckles, and elbows as practiced in conventional Acupressure and Trigger-Point therapies, (3) application of long duration of hand-touch on "safety energy-locks (SEL)," as practiced in Jin Shin Jyutsu (□□□). The present invention electronically stores the maps of life-energy pathway and gateways, such as Meridians and Collaterals, ("Jinglou," 經絡) "Acu-Points (□□)," "Trigger Points," and "Safety Energy-Locks (SEL)" (maybe simply referred to as "Points" in the remainder of this disclosure) in relation to specific health conditions.

The present invention indexes specific heath conditions to correct, proven, and authoritative charts of specifically relevant Points that treat the specific health conditions.

The present invention contemplates an electronic multi-purpose electrical and/or electromagnetic health enhancement and stimulating device that uses composite trains of alternating electric (voltage and current) pulses with varying frequencies, amplitude, wave shapes, and modulation, via pairs of conductive gel-pads with various shapes placed on skin areas above a set of Acu-points, or other Points that treat certain undesirable health condition(s), and/or help obtain desirable health conditions, according to the Traditional Chinese Medial Art of Acupuncture, Acupressure, Jin Shin Jyutsu, Reiki, Trigger Point Therapy, etc.. As long as the conductive gel-pads cover, or is near the relevant Points, the electric pulse-train in the present invention produces a self-navigating current to the precise Acu-points, to stimulate and help unblock and balance the "qi" and "shue" (micro-nutrient) flow in the Meridians and Collaterals, and Organ and Muscle Regions associated with the pair of Points. Alternately, the conductive gel-pads can be imbedded with coil shaped electrodes that would generate a magnetic field when an electrical current flows through the coil. A properly tuned magnetic field stimulates bone growth and healing.

The electronic multi-purpose electrical and/or electromagnetic health enhancement and stimulating device of the present invention contemplates the storage, retrieval and display of charts for specific sets of relevant Acu-Points, Trigger-Points, and Safety Energy-Locks (and other Points) that are used to treat specific undesirable health conditions and to help obtain/enhance desirable health conditions.

In view of the above, it is an object of the present invention to provide an electronic stimulating device that achieves competent results of Acupuncture and/or Acupressure therapies, while eliminates the use of the Acupuncture needles presently used in conventional Acupuncture therapies, and the inconvenience of applying strong thumb/elbow pressure as practiced in conventional Acupressure therapies Another object of the present invention is to provide an electronic stimulating device that can be used to apply electrical pulse-trains to Trigger Point therapies, to eliminate the need to use thumbs, fingers knuckles, or elbows to apply considerable force on the relevant Trigger Points of the patient, as practiced in conventional Trigger Point therapies.

A still further object of the present invention is to provide an electronic stimulating device that can be used to apply electric pulses to "safety energy-locks"(SEL) in Jin Shin Jyutsu therapies, in lieu, or in addition to the hand touching and holding of the relevant "safety energy-locks" (SEL).

A still further object of the present invention is to provide an electronic multipurpose electrical and/or electromagnetic stimulating device that can be used to stimulate muscle regions, nerves, and joints that reduces pain, and restores proper functioning of the muscles, nerves, and joints. The electromagnetic stimulation is known to stimulate and accelerate bone healing and growth.

A still further object of the present invention is to provide an electronic health enhancement and stimulating device with stored charts that identify a treatment method, pulse durations, pulse intensity and other relevant information. Each chart is indexed to the relevant health condition, symptoms, and related conditions in electronic memory. A respective chart and associated information can be "called-up" in real time, as needed, by a practitioner or a user, by means of entering or selecting from a menu-tree, key words of the specific heath condition or related symptoms to be treated, via an electronic input and display device. The electronic memory and the input and display device can be integrated with the pulse generation device, forming an all encompassing device system, that can display needed treatment charts, treatment methods, as well as any other useful information, by key-in or selecting from menus, the health condition and/or symptoms, and generates desired/selected/needed pulse trains. More common health conditions and the more basic treatments can be stored in hand-held/palm-top personal health enhancement and health maintenance devices. Capability to generate a small number of outputs, such as 1 to 3 outputs, can be installed in the hand-held/Palm-top devices. Larger number of outputs, and more exhaustive range of charts and information on a more exhaustive range of health conditions, and more detailed clinical information and in-depth treatment methods can be stored on clinical class devices.

A still further object of the present invention is to provide an electronic health enhancement and stimulating device that is programmable, and includes pre-programmed, menu selectable, and default sequences/trains of varying electric pluses, with varying frequencies, amplitudes and modulations, such that the person treated does not get "trained-to"/"used-to" an unchanging stimulus and cease to respond.

BRIEF DESCRIPTION OF THE DRAWINGS

FIGS. 1A to 1D illustrate examples of Meridians, locations of Acu-Points on the Meridians, and examples of "indications," the health conditions and symptoms each Point treats in accordance with known art.

FIG. 2 illustrates charts and indications of the 26 pairs of Safety Energy Locks (SEL) in Jin Shin Jyutsu in accordance with know art wherein only one SEL of each left-right symmetry pair is shown.

FIGS. 4A to 4C illustrates examples of displayed charts on the electronic enhancement and stimulating device and the electronically stored relevant Acu-Points data for treating specific health conditions wherein each chart is indexed to the health condition it treats and symptoms of the health condition.

DETAILED DESCRIPTION OF THE EMBODIMENTS OF THE INVENTION

The present invention discovers that a properly designed train of low frequency and low voltage electrical pulses in the order of 0.5 Hz to 200 Hz, 3 Volts to low tens of Volts, applied via a pair of conductive-gel pads placed over the skin area above (or very near to) a pair of Acu-Points (FIGS. 1A–1D), results in a well-defined electrical current drawn through the pair of Acu-Points, exactly at the points, into the body. The current ranges in the order of a few mAmps to up to the order of 200 mAmps, coursing through an energy pathway between the two points. The same effect also occurs with a pair of Trigger Points (FIGS. 3A and 3B), the Safety Energy Locks (FIG. 2), and Points in the Muscle regions, across joints, and near or along branches of nerves.

Figure 1A:
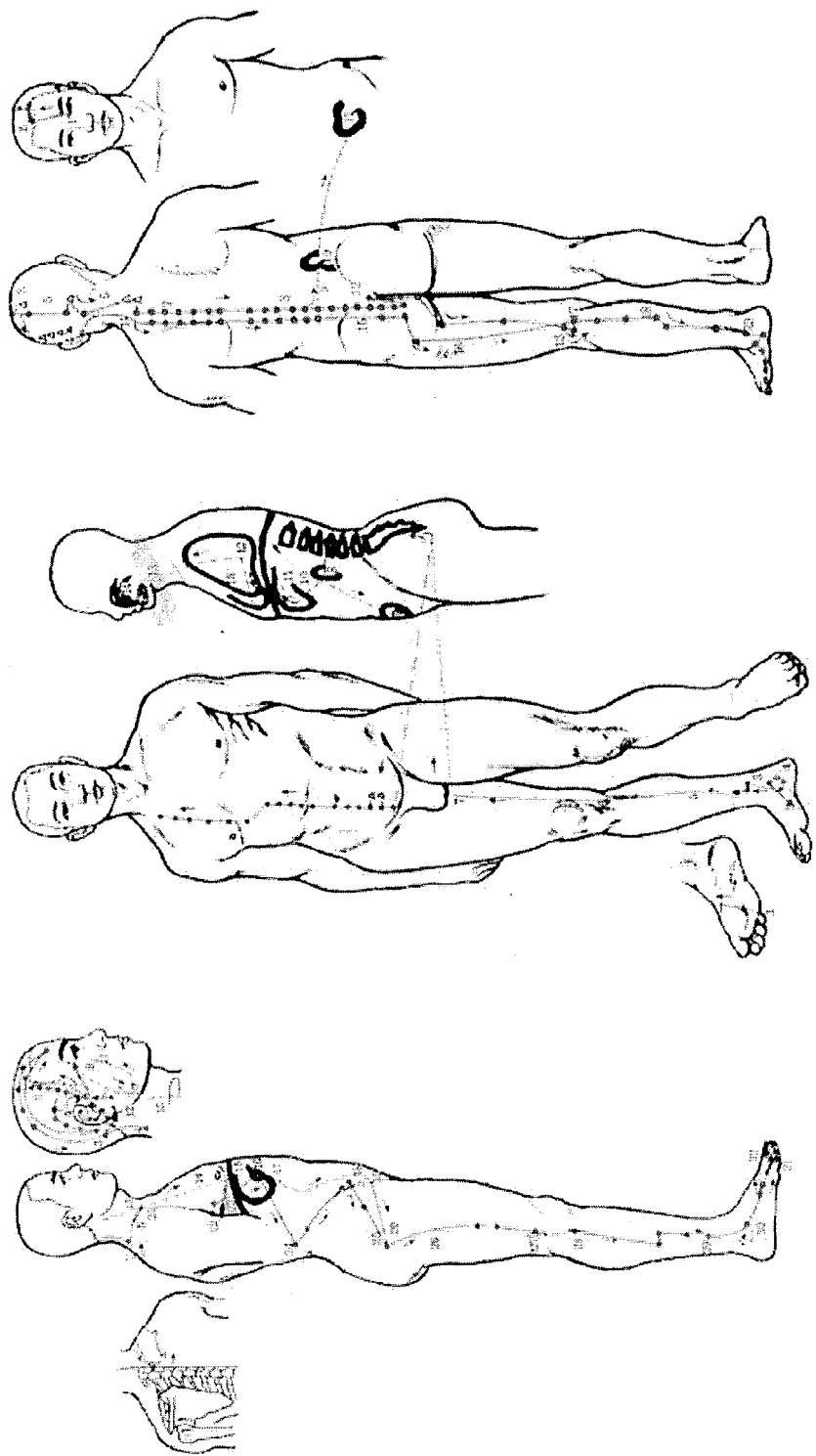
Figure 1B:
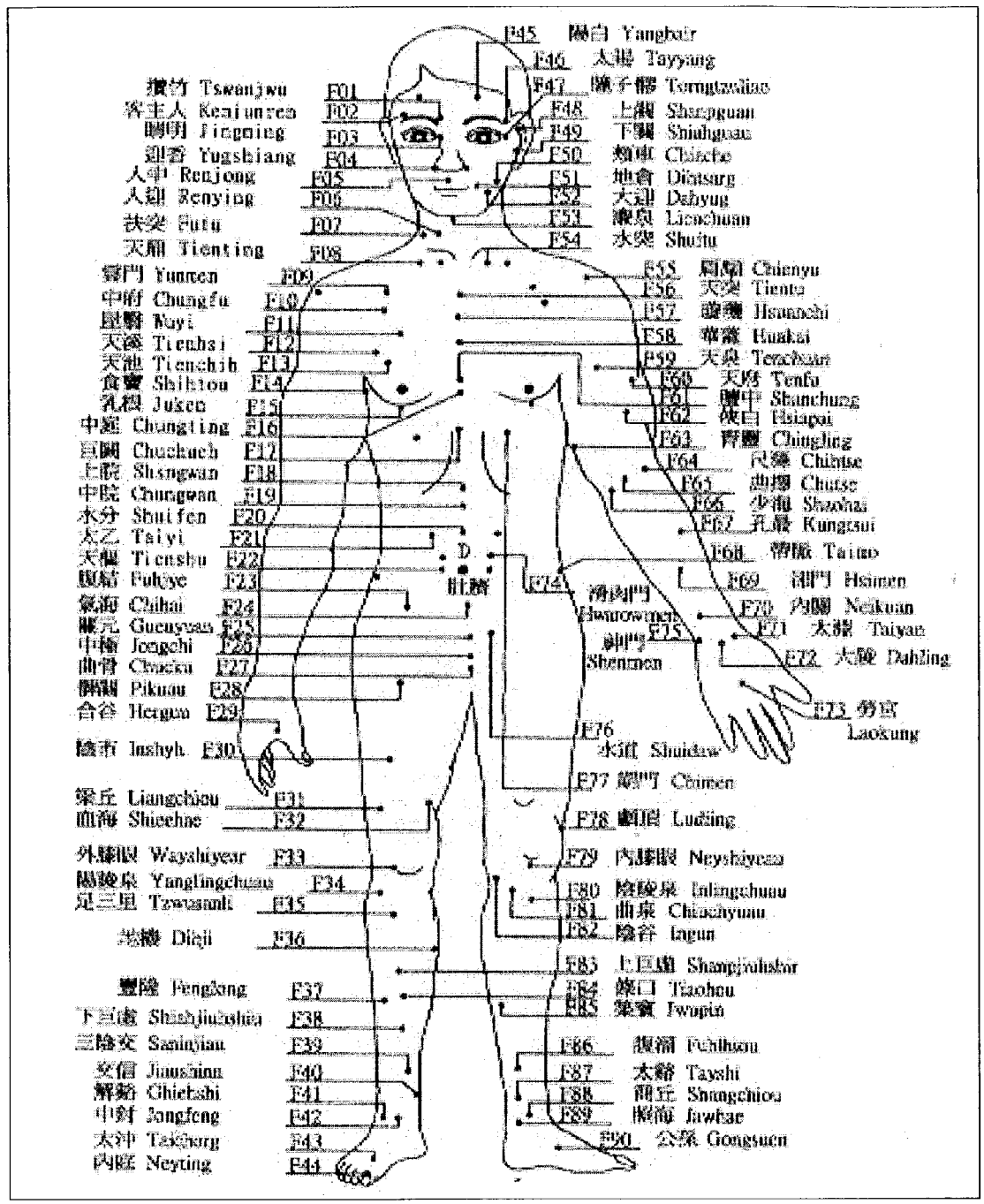
Figure 1C:
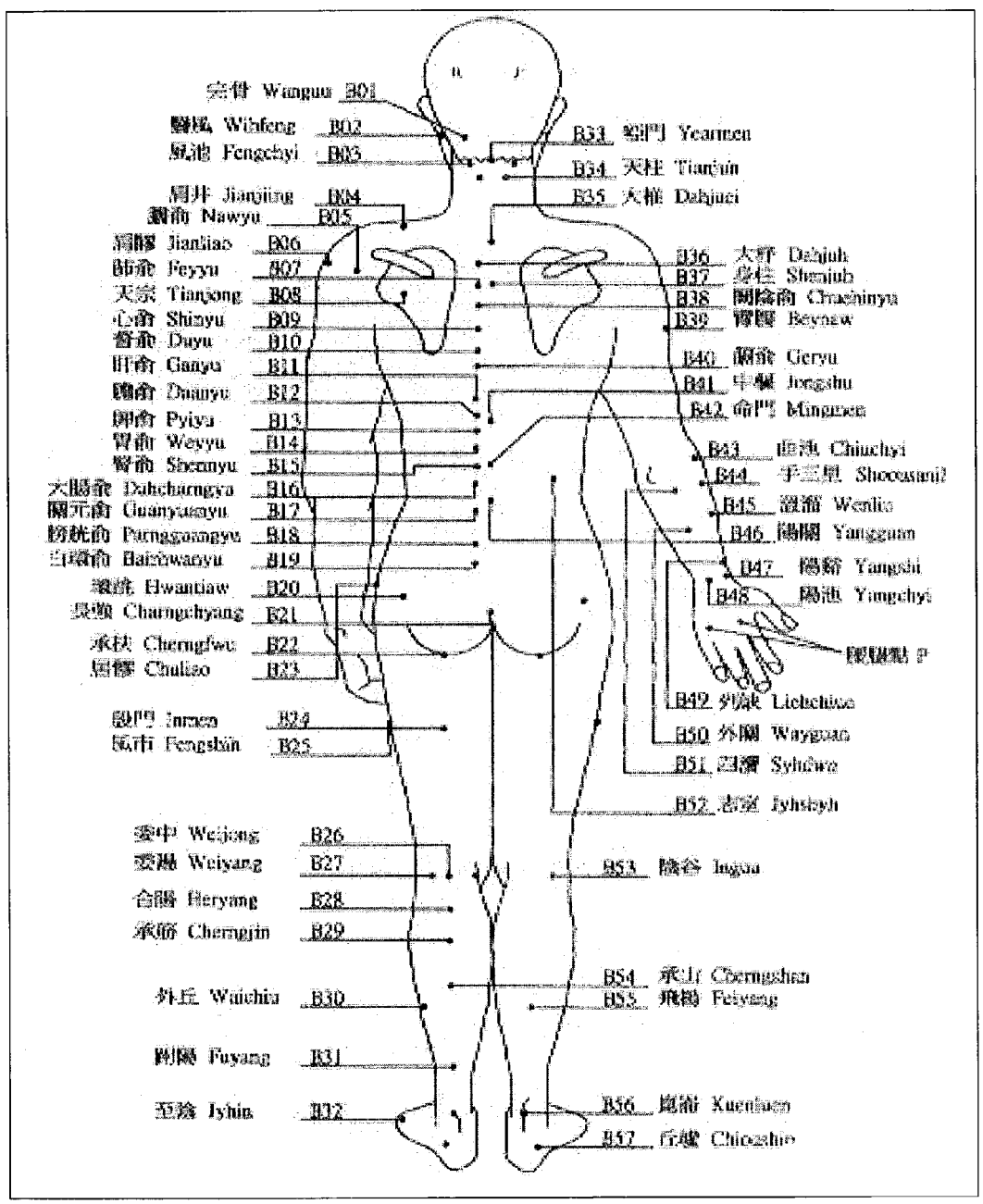

FIG. 1A charts 3 (three) of the 32 Meridians:the Gallbladder Meridian of Foot-Shaoyan, which contains 32 Points; the Kidney Meridian of Foot-Shaoyin, which contains 27 Points; and the Bladder Meridian of Foot-Taiying, which contains 67 Points. FIGS. 1B and 1C charts the positions, the names, and a rudimentary international numerical conventions of major frontal and backside Acu-Points. Except for the Acu-Points located along the front and back central axis of the body, all Acu-Points are in pairs of left-right symmetry. For economizing space and readability, FIGS. 1B and 1C indicate only one point from each symmetry-pair. A more sophisticated International numerical convention developed by the Chinese Academy of Traditional Chinese Medicine notates the Acu-Points with the first initial of the name of the Meridian where the Acu-Point is located, as shown in FIG. 1D. FIG. 1D also lists names of the Acu-Points along with the "indications" (the health condition and symptoms that can be treated through the Point) of 12 of the 27 Acu-Points along the Kidney (K) meridian of Foot Shaoyin.

The present invention contemplates compiling the relationship of the Points and their "Indications" differently and more conveniently: the names of health conditions as the headings, while the symptoms, pathological and clinical information of each health condition, and the Points that can be used, or need to be treated for each health condition are listed under the health condition heading, as exemplified in FIG. 4s.

FIG. 2 illustrates locations of the 26 left-right symmetry pairs of Safety Energy Locks (SELs) in Jin Shin Jyutsu, as well as the SELs useful in treating areas of the body, and various health conditions.

Figure 3A:
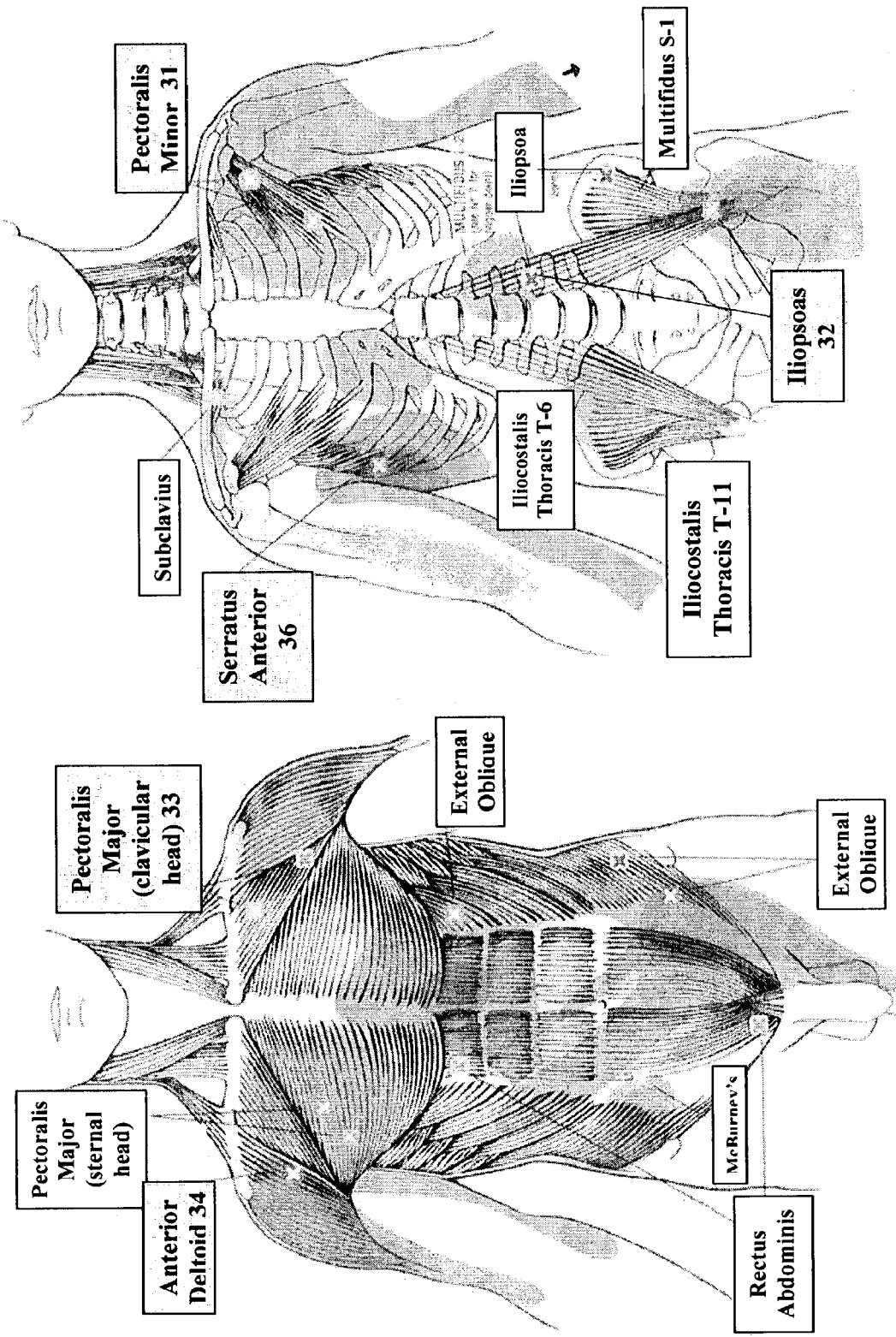
FIGS. 3A and 3B illustrate exemplary charts of Trigger Points, and examples of pairs of Trigger Points where electrodes are to be applied in accordance with the present invention.
Figure 3B:
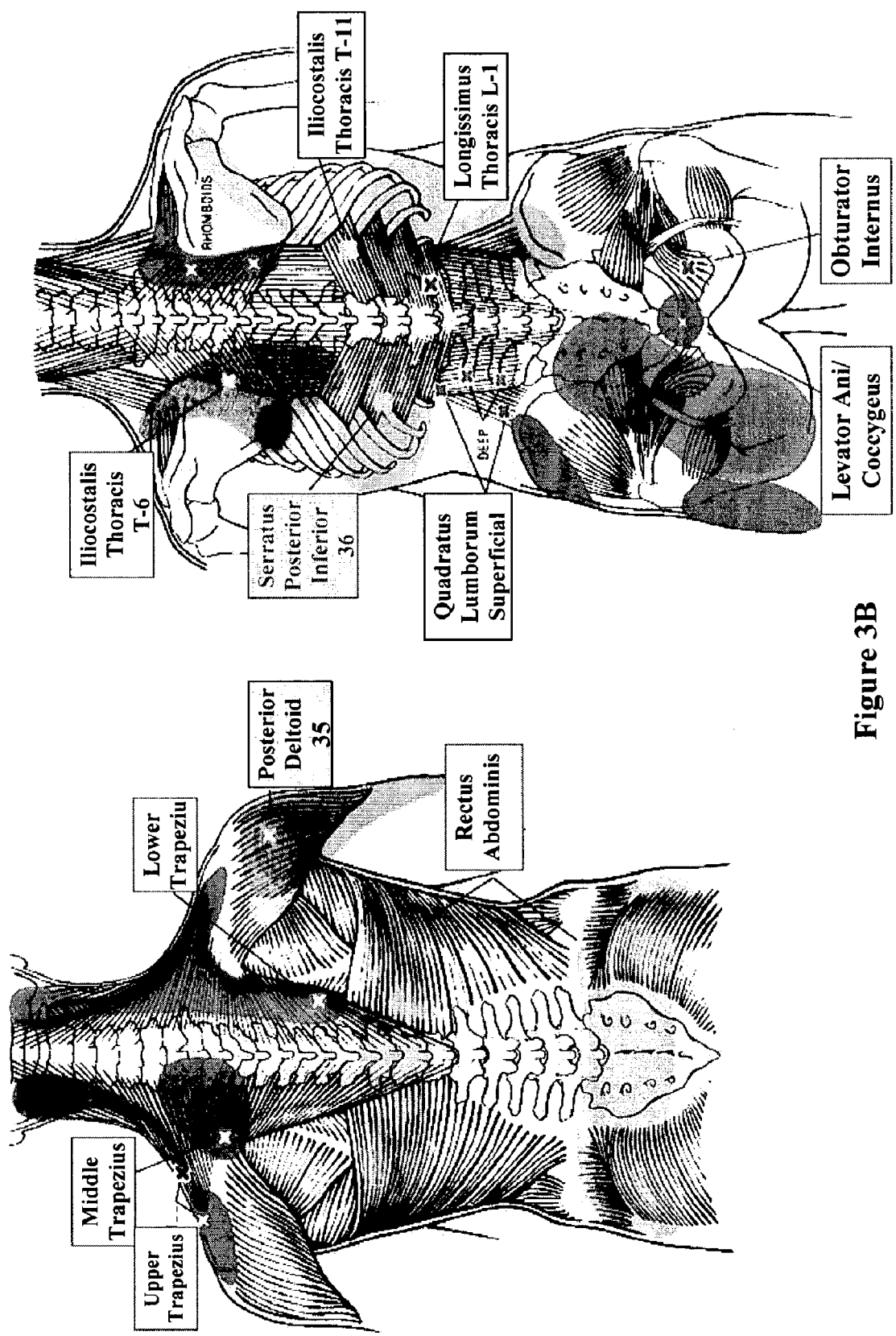

FIGS. 3A and 3B show the locations of some of the Torso Trigger-Points. FIG. 3A is the front-torso Trigger-Points and FIG. 3B is the back torso Trigger Points. An "Xt" indicates a Trigger Point. A darker shaded area around the Trigger Point indicates the primary muscle tissue associated with the Trigger Point. The lighter shaded area indicates the secondary muscle tissue associated with the Trigger Point. The Trigger Points coincide with a subset of the Acu-Points in the Muscle Regions.

The electronic health enhancement and stimulating device eliminates: (1) the needle-insertions as practiced in Acupuncture, (2) the use of hands and fingers as in Jin Shin Jyutsu, (3) the use of thumbs, knuckles and elbows to apply pressure as practiced in Acupressure and Trigger Point therapies. Instead, the electronic health enhancement and stimulating device uses electrical pulse-trains applied via conductive gel-pads on the skin areas over the relevant Acu-Points, SELs, or Trigger Points to deliver results superior to Acupuncture, Acupressure, Jin-Shin Juytsu, Trigger Point, Reiki, as well as many other therapies.

For the Trigger-Point therapy, the embodiment of this invention is to place the conductive gel-pads on the skin area directly above a pair of Trigger Points in the muscle region to be treated, for example, as illustrated in FIG. 3A, Pair 31 for Pectoralis Minor, Pair 32 for Iliopsoas, Pair 33 for Petoralis Major, Point 34-the Anterior Deltoid in FIG. 3A and Point 35-the Posterior Deltoid in FIG. 3B for Deltoids, and Serratus Anterior 36 in FIG. 3A and Serratus Posterior 37 in FIG. 3B for Serratus.

Another embodiment of the electronic multipurpose electrical/electromagnetic health enhancement and stimulating device in accordance with the present invention graphically charts specific groups of relevant Acu-Points/SELs/Trigger-Points for treating a specific health condition. Each chart is then recorded along with treatment method and other relevant information, and indexed to the health condition and symptoms it treats. This embodiment eliminates the difficulties in looking up the relevant treatment Points from a reference book or text book, and then locating the Point positions from the traditional whole-body charts as shown in FIGS. 1A–1D and 2, where a large number of irrelevant Points are also present. The Charts of the present invention may include a limited number of useful reference Points to help locating the precise location of the relevant Treatment Points.

Figure 4B:
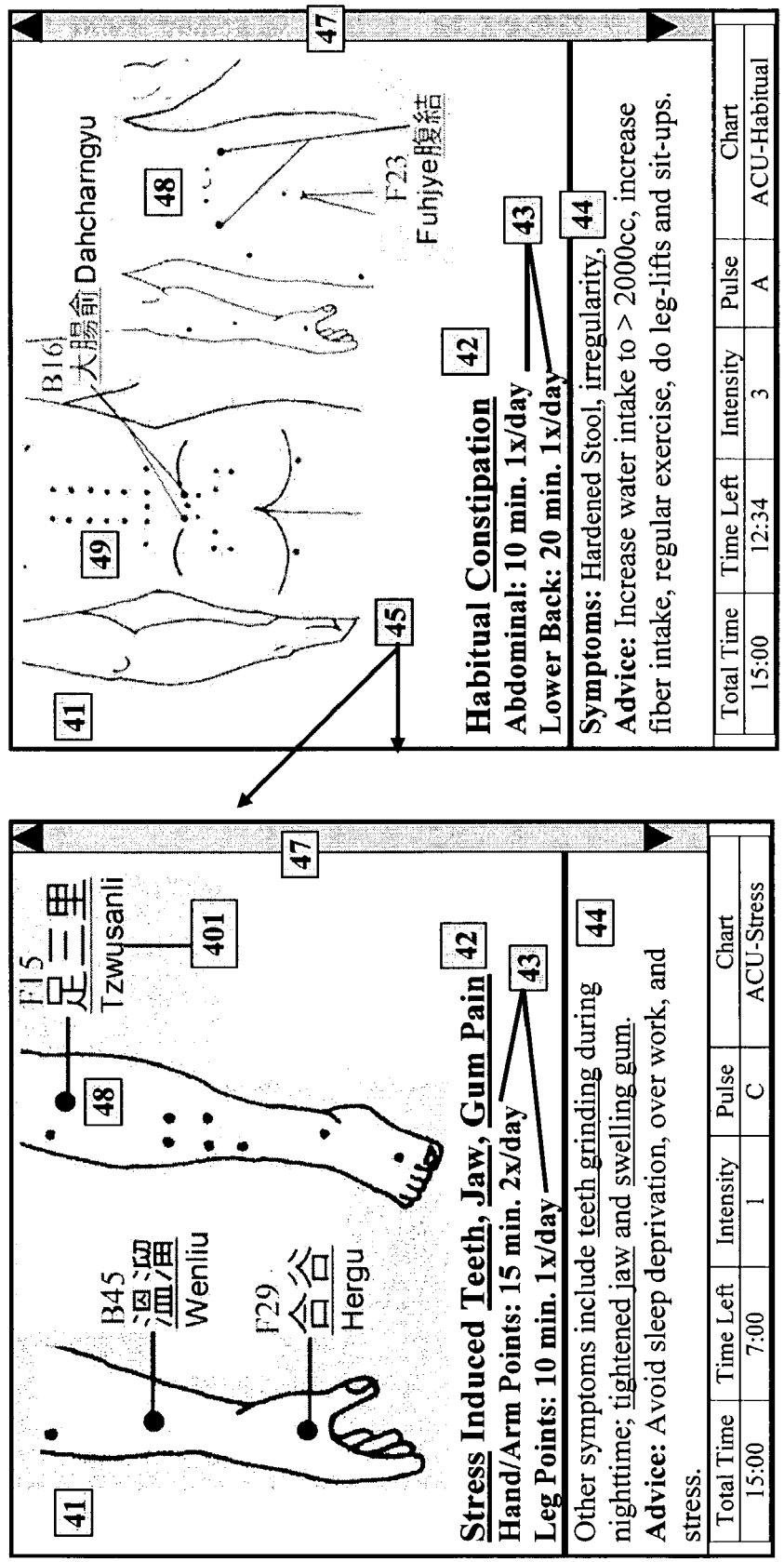
Figure 4C:
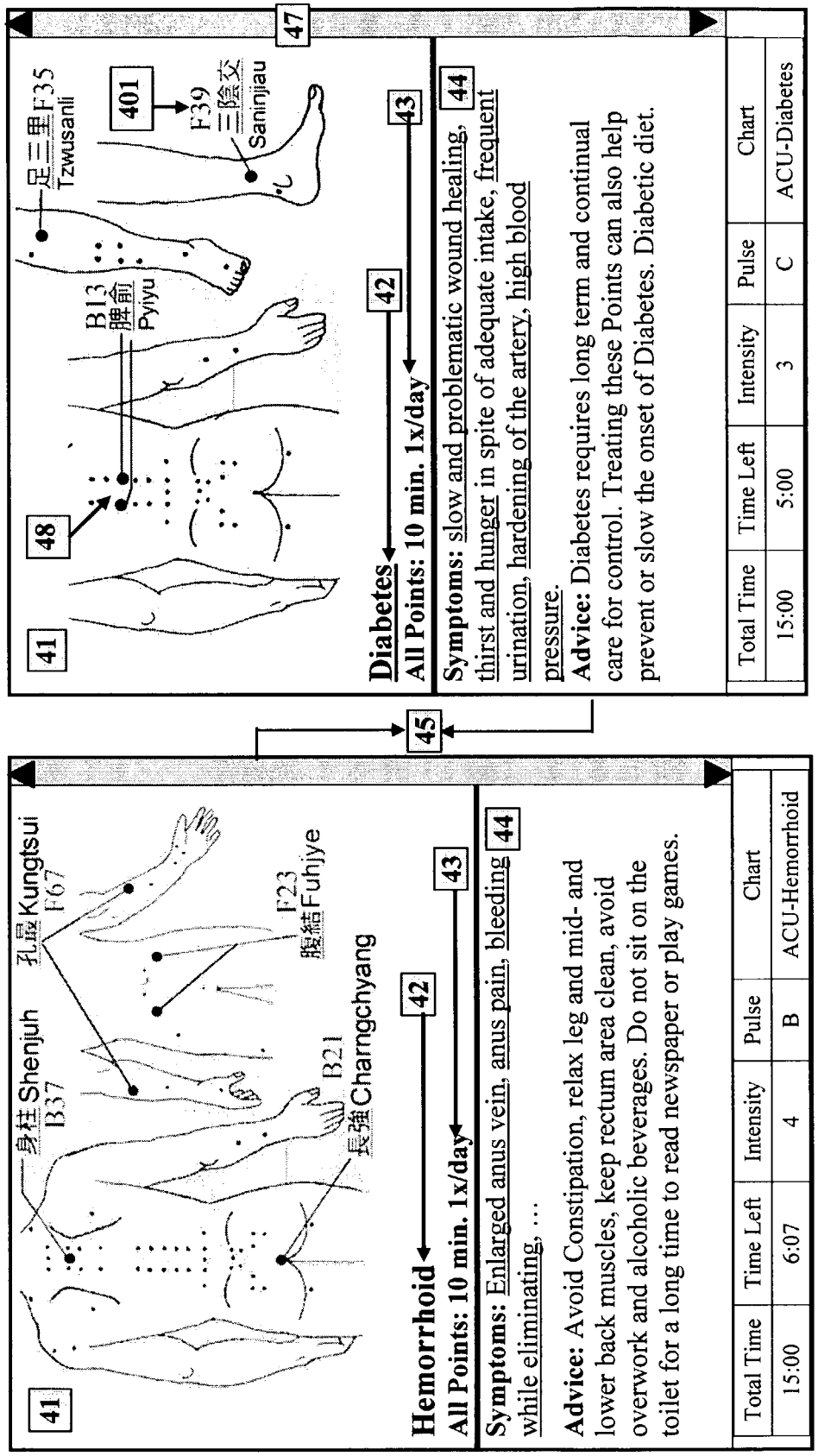

FIGS. 4A through 4C illustrate exemplary charts 41 for Acu-Points. The charts are then stored in electronic memory, indexed to the specific health condition 42 and/or symptoms, along with treatment method and duration 43. A needed chart can be called up on-demand in real-time by a user, to display on an electronic display screen 45, via entering key word(s) (42, 44) of, or selecting from a menu, the specific health condition 42 or symptoms 44 to be treated. The "Taking Points" 48 (e.g. Treatment Points) are differentiated from "Reference Points" 49 by larger "Point" size, and/or color, as well as the labeling of the "Taking Points" (or Treatment Points, the set of Points that can be, or should be used to treat a health condition) with their names, such as the Chinese symbols and the corresponding phonetic translations and numeric notations 401. The scroll bar 47 allows more information to be stored and displayed by scrolling the page content up and down through the display window.

The relatively large size of the conductive gel-pads used to administer electrical currents relaxes the precision of locating the Treatment Points. As long as the Treatment Points are covered under the conductive gel-pads, the electrical current self navigates to the Treatment Points. If a Treatment Point is near, but not near enough to the edge of a conductive gel pad, a somewhat ill defined sharp, needling, and less comfortable sensation around the Treatment Point, is produced by the ill-defined current flow. This is in contrast to a very well defined, strong, yet very comfortable sensation of a strong, and well-defined current flow when the Treatment Point is directly covered under the conductive gel-pad. By moving the conductive gel-pad toward the "needling" point on the skin, to better cover the Treatment Point, the ill defined and somewhat uncomfortable current-flow sensation will change to that of a well-defined and comfortable current-flow sensation.

The health enhancement and stimulating device of the present invention enables effective self-administration and/or administration by a friend or a family member, health enhancing and pain-relieving therapies to alleviate, improve, or prevent chronic health problems, without the side-effects, long-term toxicities, and expenses of using drugs on a long-term basis.

Practitioner practicing the conventional methods can also use the charts of the present invention and the health enhancement and stimulating device to help find the exact location of a Point, via electrical-probing, and to administer therapies. Alternately, the charts can simply be printed in a quick-instruction manual, with tables of contents and indices. Such quick-instruction manual is easier to use then the conventional textbooks, reference books, and reference charts.

Alternately, the precise location of a pair of Treatment Points can be detected by a current sensor that measures the current drawn between two probe tips placed on skin areas close to a pair of Treatment Points as indicated by the Chart. By gliding the probe tips in the vicinity, an optimal reading is obtained when the probe locations are precisely over Treatment Points.

If either or both conductive-gel pads of the two poles (one output) of an electrical pulse train cover more than one pair of Acu-Points, the pair of Acu-Points, one under each of the conductive gel-pads that are connected to a Meridian would draw the current, while unconnected Points are not affected.

If more than one pair of points are connect to one or more than one Meridian, the section of the Meridian (or the Meridian) that is associated with a most (or more) pronounced existing health condition, would draw most (or more) of the electrical current.

Figure 5:
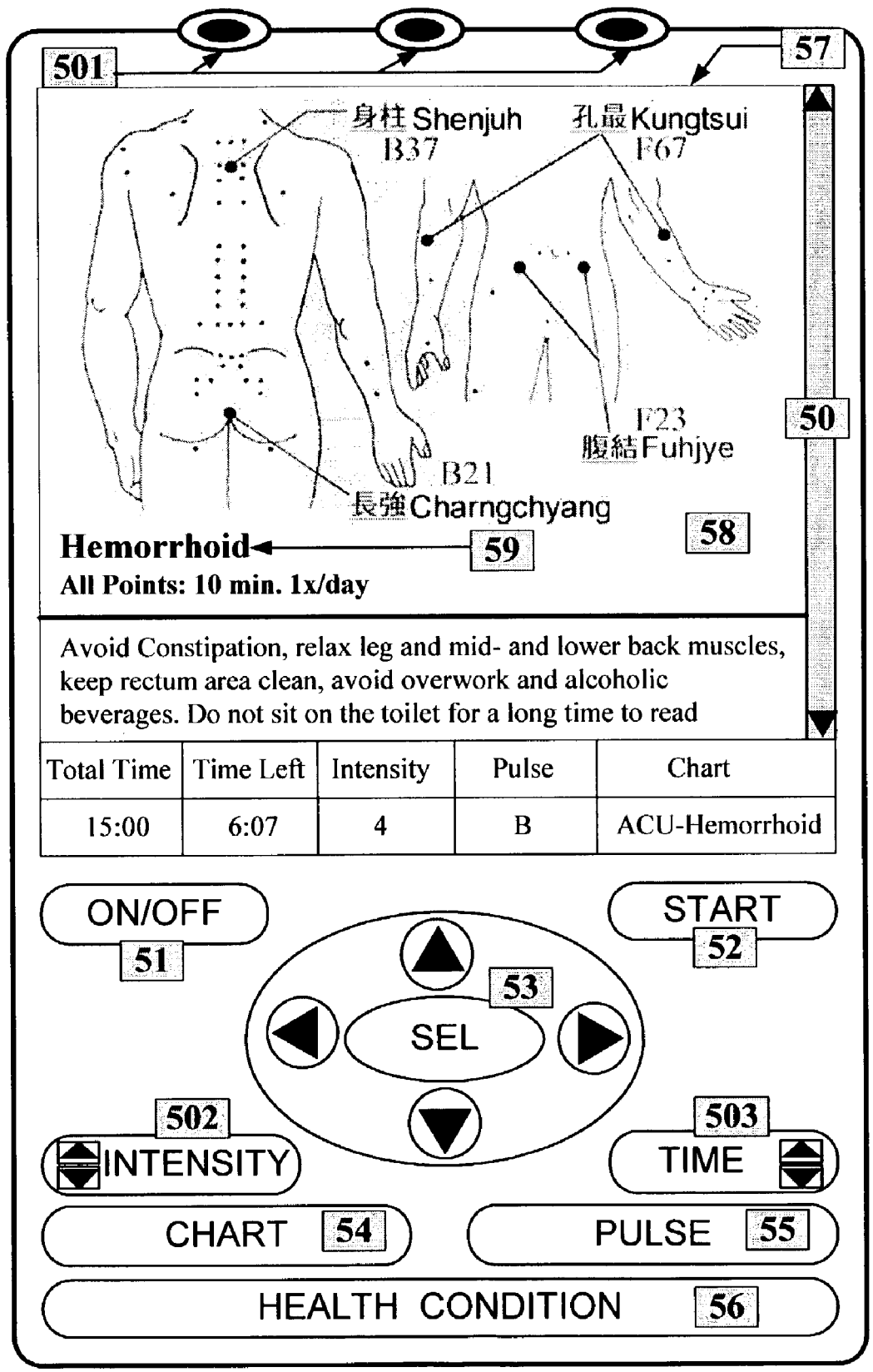
FIG. 5 illustrates an electronic health enhancement and stimulating device of the present invention employing a "clip-on/palm-top/pocket size device."

The next embodiment of this invention integrates/embeds the electronically stored charts and the display device in an electronic pulse-generation device that supplies the pulse-trains in the first embodiment. The nature of the low voltage, low frequency, and low power of the pulse trains allows the entire integrated device to be highly portable, while supplying multiple outputs. A hand-held/clip-on/palm-top implementation of embodiments of this invention is illustrated in FIG. 5. An On/Off button 51 turns the device "on" and "off." The group of buttons 53 surrounding the Selection button SEL, enable the user to step through the display and menus, to select desired menu and the desired chart and information to treat a particular health condition. The CHART button 54, when pressed, calls for the menu of the stored charts to be displayed on the display screen 57, such that the user can step through the menus to select the desired chart. The scroll bar 50 scrolls the display content up down the display screen for viewing. The PULSE button 55, when pressed, calls for the menu and instructions for selecting or programming an electrical pulse-train to be used, such that a user of the device can step through the menu tree until a desired pulse train is selected or programmed. Pressing the START 52 button would command the device to supply selected pulse trains to the OUTPUTS 501. If a user press the START 52 button after a specific chart 58 for a specific health condition 59 is selected, default pulse-trains would be supplied to the output leads 501. Pressing the INTENSITY 502 rocker-button up, or down would increase, or decrease the pulse-train intensity. Pressing the TIME 503 rocker-button up, or down would increase, or decrease the total treatment time. A pulse-train stops when the total treatment time programmed for that pulse-train is reached.

The number of Treatment Points for a certain health condition most often range from 2 to 5 pairs. Several health conditions are often related to each other, or are causes and effects to one another. The related conditions should be all treated to obtain optimal result. For example, diabetes could cause hardening of the arteries, high blood pressure, arthritis, impaired eyesight . . . etc. Therefore, it is desirable to stimulate Treatment Points not only of a particular ailment—such as diabetes, but also Treatment Points corresponding to the related ailments—such as impaired eyesight and arthritis. This invention supplies multiple sets of outputs and electrodes, such that multiple pairs of Points can be stimulated at the same time, which dramatically reduces treatment time needed, and increases the treatment effect. The present invention builds multiple outputs to a single portable device; each output is cabled to a pair of conductive gel-pads or other forms of bi-polar electrodes, so that multiple electrical currents can be drawn to treat multiple pairs of Acu-Points or Trigger-Points simultaneously to cut down total treatment time needed by many folds.

Figure 6:
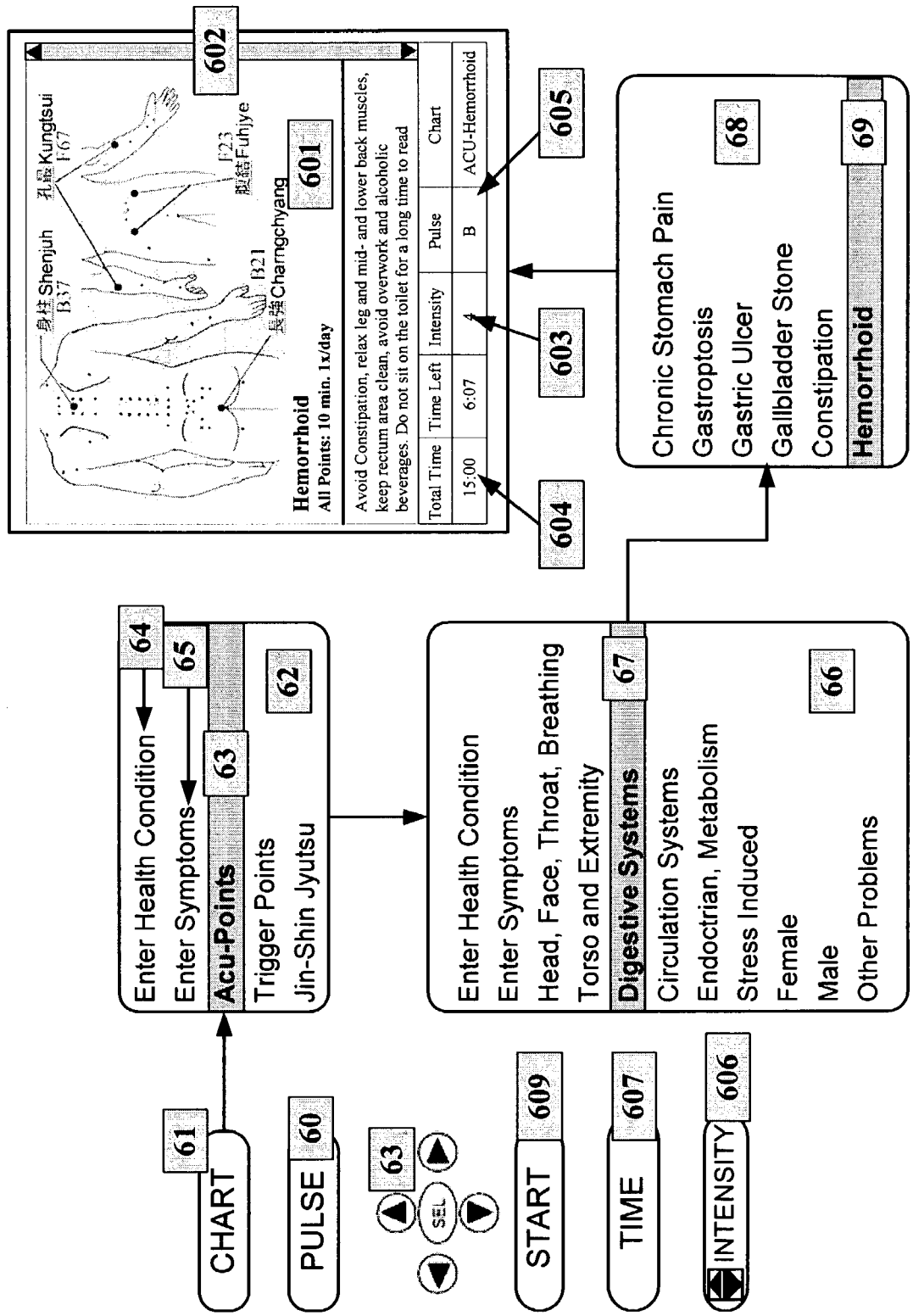
FIG. 6 illustrates a general block/flow diagram and a clinical version of the electronic health enhancement and stimulating device in accordance with the present invention.

The treatment charts can be called onto the display on the pulse-generation device, on-demand, in real-time via input keys and/or menu-selection. FIG. 6 illustrates an example of a menu-selection method/process to access a specific electronically treatment chart. When a user presses the CHART button 61, the first level menu 62 is displayed (on the display screen 57 of the device as shown in FIG. 5). Using the arrowed buttons in the group of SEL (selection) buttons 63, a user can step the highlighted/shaded cursor bar 63 up or down (or left or right) on the menu, to the desired selection, and then press the SEL button at the center of 63 to fix the selection. For example, if either the Enter Health Condition 64 or Enter Symptoms 65 are selected, an on screen keyboard and an on-screen text entry box may appear to allow the user to enter the key word(s) of the name of a health condition to be treated or its symptoms. Pressing SEL button again, would then bring up the Treatment Chart for that health condition. If the key word(s) entered are ambiguous, and indices of multiple charts are identified to contain the keyword(s) entered, a menu of the names of the health conditions of these charts would be called up from the electronic memory, and displayed on the display screen for the user to identify the exact chart he/she wants. Now the user shifts the highlighted/shaded selection cursor bar 63 to Acu-Points, and press the SEL button, the health-condition based hierarchical menu 66 for Acu-Point Charts would appear. To illustrate the process further, we now step/shift the highlighted/shaded selection cursor bar to Digestive Systems 67, and press the SEL button. The next level menu 68 would be called up from the electronic memory, and displayed. We now step/shift the highlight bar to Hemorrhoid 69, and press SEL. The chart of the Treatment Points for Hemorrhoid, along with treatment method and other relevant information 601 are called from the electronic memory, and displayed on the display screen. The group of Shift and Select buttons 63 are also used to shift the highlight/shaded cursor bar, to the right or left, for example, to the scroll-bar 602 to scroll the information displayed on the display screen up and down the screen. If the START 609 button is pressed at this time, a set of default electrical pulse trains at a default Intensity 603 setting, would be supplied to the OUTPUT leads 501 in FIG. 5. If a user desires stronger electrical pulse intensity, he/she may use the group of Shift and Select buttons 63 to shift the highlighted cursor to Intensity 603, and press the SEL button. The available levels of Intensity, such as 1 through 10 (or 1 through 15), could then be chosen via pressing the up or down buttons in 63. The options can also be displayed on the screen for user selection using the highlighted cursor bar. Alternatively, an INTENSITY 606 rocker button can be implemented to accomplish the same purpose by rocking the button up or down. Similarly, the user can select the total treatment time by shifting the cursor to Total Time 604 or using the device button TIME 607. To select or program the pulse-train to be used, a user shifts the cursor to Pulse (605), or us the device button PULSE 60.

Figure 7:
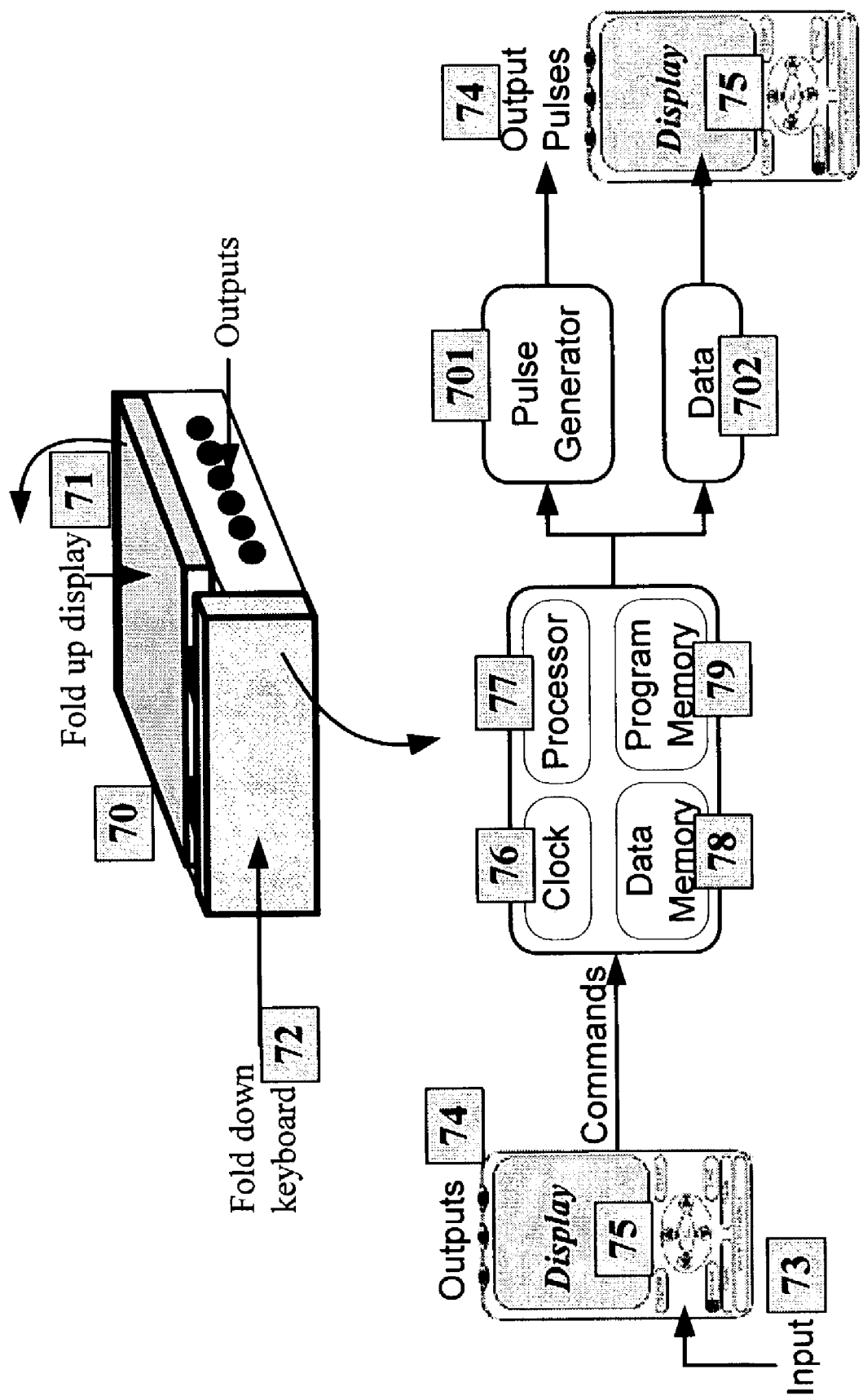
FIG. 7 illustrates an example of a menu selection method for calling for the Point Chart and treatment method for a specific health condition—such as Hemorrhoid, to display on a palm-top device in accordance with the present invention.

Larger clinical device as shown as 70 in FIG. 7 can be implemented to contain a larger number of outputs, larger display 71, and a keyboard. The display and keyboard can be designed to pull/fold up/down from the main body of the device. More sophisticated programs and more detailed and exhaustive information and treatment methods for a much larger range of usual and unusual health conditions can be incorporated and stored in a larger clinical device with a larger processor and larger electronic memory. The clinical version can greatly enhance the reliability, quality, and consistency of treatments administered by clinical practitioners, who conventionally depend on his/her ability to recall at treatment time, his/her knowledge, experience, and memory. This instant-recall ability of practitioners varies from time to time, the stress conditions, and from individual to individual.

FIG. 7 also illustrates the functional block diagram of the embodiments of the present invention. The functional blocks are similar between a clinical version and a hand-held/palm-top version: input 73, output 74, display 75, clock 76, processor 77, program memory 79, data memory 78, and pulse generator 701. The needed data 702 called up by commands entered via Input 73 and/or menu-selection from Display 75, would be shown on Display 75. The pulse-trains as specified via Input procedures, or the default pulse-trains, would be supplied to the Outputs 74.

Figure 8A:
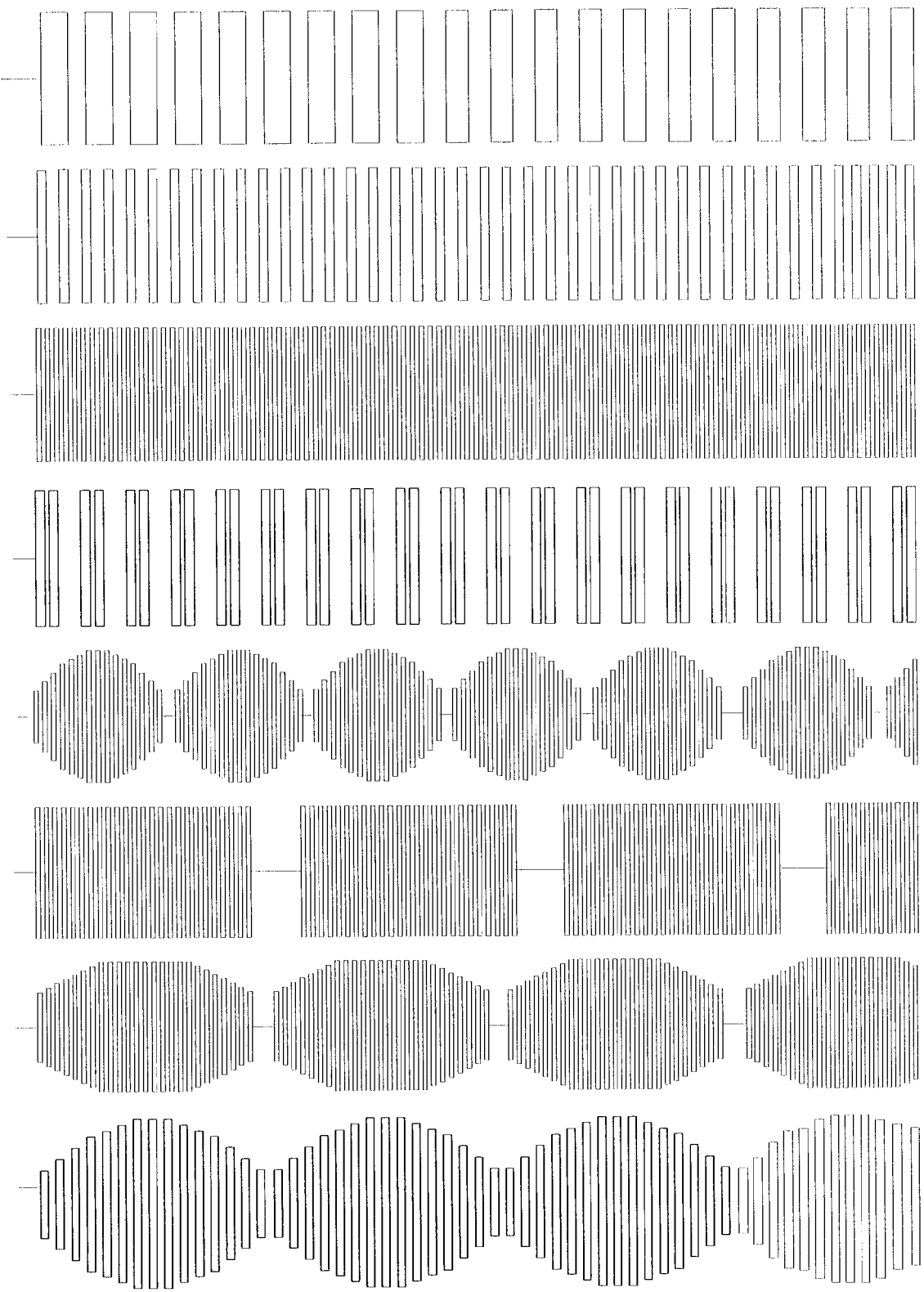
FIGS. 8A and 8B illustrate Electrical Pulse-Train Examples: 8 component examples and one composite combination example in accordance with the present invention.
Figure 8B:
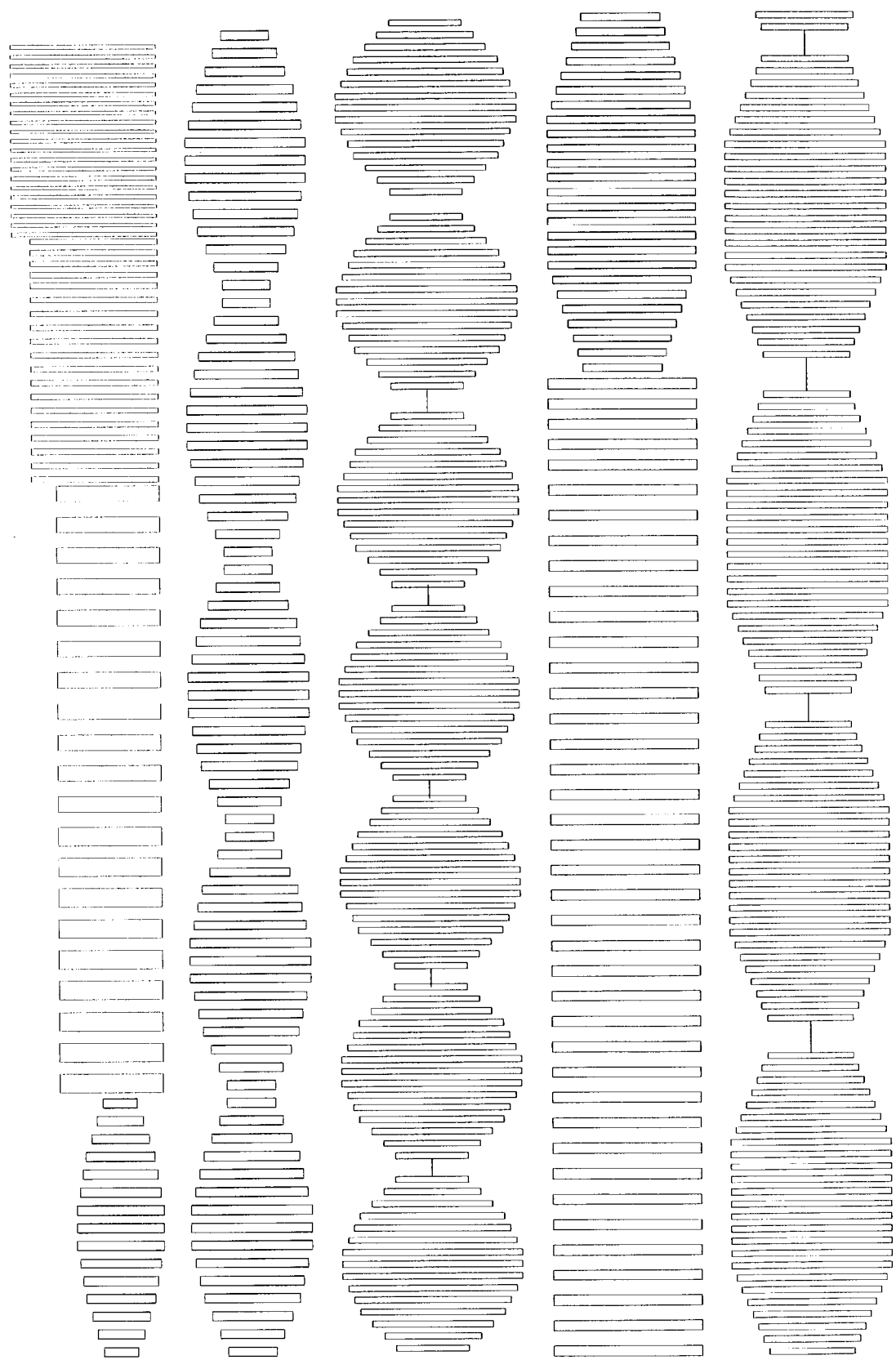

Another embodiment of the present invention is to provide pulse trains of varying wave shapes, frequencies, modulation, and amplitude throughout the treatment duration, to avoid the tendency in biological subjects to become "used to" an unchanging stimulant and fail to respond. FIG. 8A illustrates examples of 8 different component pulse-trains of different frequencies, modulations, and pulse shapes. FIG. 8B shows one example of a varying pulse-train using a combination of component pulse-trains. Various combinations of these component pulse-trains can be preprogrammed as defaults and selectable options.

Figure 9:
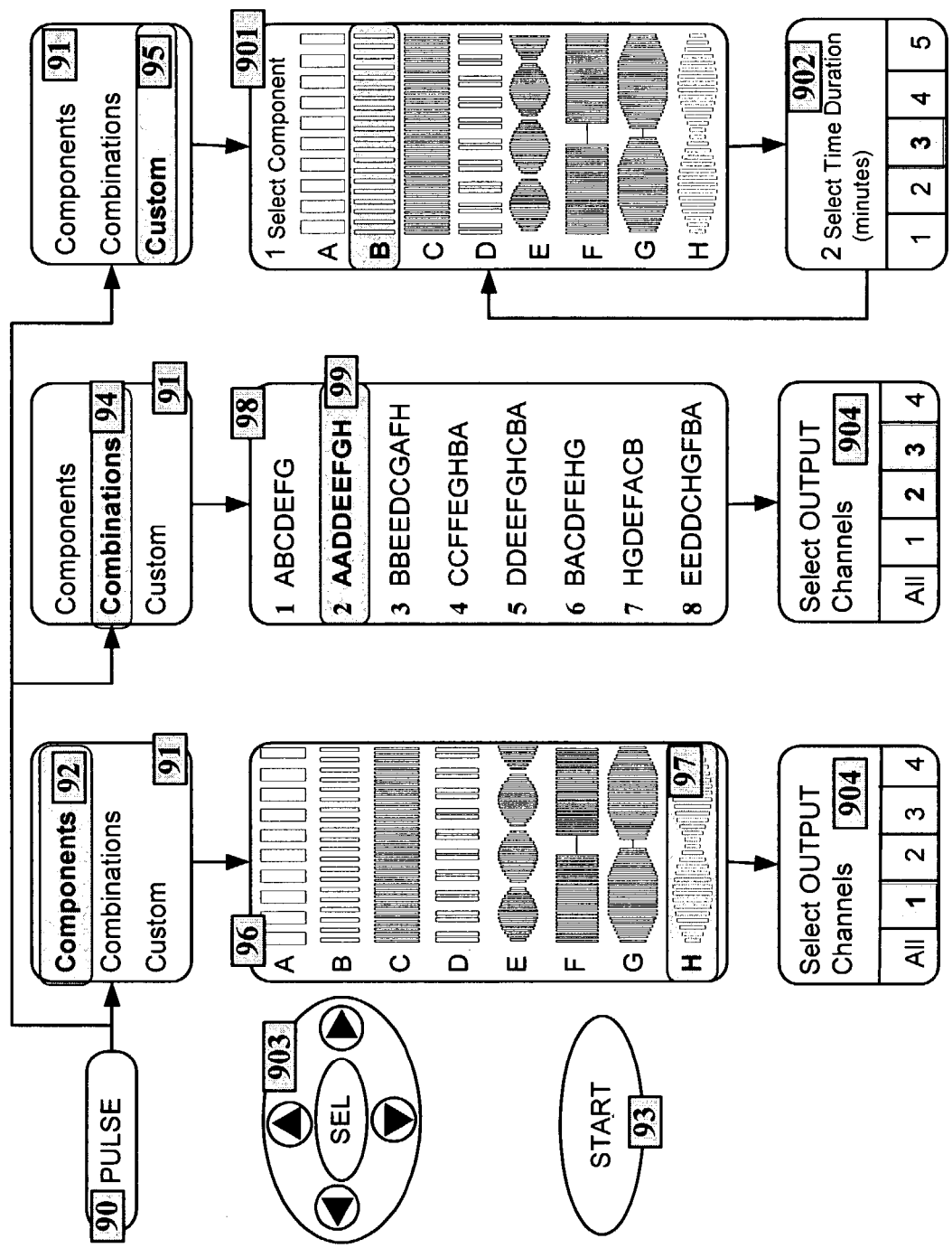
FIG. 9 illustrates an example of a menu selection method for calling up a desired pulse-train in accordance with the present invention.

An additional embodiment of this invention is to facilitate user selection of components or combination pulse-trains, and provide user programmability for custom combinations of component pulse-train to compose custom treatment pulse-trains. FIG. 9 illustrates an example method/process for pulse-train selection and programming. Individual output pulse selection can be performed individually one-at-a-time. Or, one selection can be applied to a number of, or all of the OUTPUTs 501 in FIG. 5.

In operation, when PULSE button 90 is pressed, the first level menu 91 appears on the display screen: Components 92, Combinations 94, and Custom 95. If the user selects Components 92, the available component waveforms 96 are displayed on the screen for the user to choose from. If the user chooses to use anyone of the component waveforms, he/she shifts the highlighted selection cursor bar 97 to the desired component pulse-train. Then, pressing SEL 903 and START 93 buttons causes the selected component voltage pulse-train to be supplied to one, some, or all of the OUTPUTs 501 in FIG. 5, as desired. The selected pulse-train repeats itself through the duration of the treatment period. Restarting the PULSE selection process would program the pulse train for the next OUTPUT (s).

In operation, when selecting Combination 94 from the menu, the available preprogrammed combinations 98 are shown on the display for user review and selection. When one particular combination 99 is selected by pressing the SHIFT buttons in 903, its waveform would be graphically shown on the display screen. The user can change selection at this point, until he/she is satisfied with the waveform he/she sees. The output channel menu 904 is used to select the OUTPUT (s) (501 in FIG. 5), where the pulse-train is to be supplied to.

Pressing START 93 button issues a command to supply the chosen combination waveform to all or the chosen OUTPUT(s). Selecting Custom 95 causes a menu 901 of component pulse waveforms to display, for custom programming. The user loops through the component selection process for each segments and the time duration 902, and Intensity (not shown here, for the process is similar to the time duration selection) for the segment until satisfied. The programmed composition pulse-train is repeated through the total treatment period. Stepping through the pulse selection process for each output can facilitate different pulse-train for each of the multiple outputs. If the START 93 button is pressed twice before all of the outputs are programmed, remaining outputs are supplied with the last selected/programmed pulse-train by default.

In summary, the merits of present invention include, but are not limited to: replacing and delivering superior result than the conventional acupuncture, acupressure, Jin Shin Jyutzu, and Trigger Point therapies, and other massage therapies, (2) the elimination of the precision needed and risks involved in inserting needles into Acu-Points as practiced in the conventional Acupuncture treatment. Furthermore, the present invention can be used to apply electrical Acupressure and Trigger-Point therapies far more conveniently, economically, and time and result efficiently comparing to the conventional practices. The effect of the conventional Acupuncture, Acupressure, and Trigger-Point therapy is highly dependent on the skill, memory, and knowledge and experience level of a particular therapist. With the present invention, the electronically stored correct and proven Expert Treatment Charts, safety voltage and current limitations, the relatively large size of the conductive gel-pads, and the self-navigating properties of the electrical currents, enable dependable and safe self-administration and/or consistent and dependable performance of therapists/operators with limited training and experience. By applying sequences of varied frequencies, amplitudes, pulse-shapes, waveforms, and modulations, The present invention bypasses the natural tendency of biological subjects in becoming "trained to"(or "used to") an unchanging stimulus which may result in failure to respond.

The present invention can also be used to stimulate muscles, joints and nerves at predetermined set of Locations for each muscle region, each joint, and nerves commanding the muscles and joints, to reduce pain, improve circulation, and restore function.

Numerous modifications to and alternative embodiments of the present invention will be apparent to those skilled in the art in view of the foregoing description. Accordingly, this description is to be construed as illustrative only and is for the purpose of teaching those skilled in the art the best mode of carrying out the invention. Details of the embodiment may be varied without departing from the spirit of the invention, and the exclusive use of all modifications which come within the scope of the appended claims is reserved.

What is claimed is:

1. An electronic stimulating device comprising:
   an electronic memory storing a plurality of health conditions and a plurality of charts identifying anatomical points for treating the health conditions, the anatomical points being selected from a group consisting of acupuncture points, acupressure points, trigger points and Jin-Shin Jyutsu points;
   an electronic indexer for indexing each health condition of the plurality of health conditions to a chart of the plurality of charts identifying the anatomical points for treating said each health condition;
   an input unit for selecting trains of electrical pulses associated with the charts;
   a plurality of pads, each pad of the plurality of pads comprising an imbedded coil-shaped electrode configured to generate magnetic field in response to electrical current;
   a pulse generator for generating the selected trains of electrical pulses and applying the selected trains of electrical pulses to the coil-shaped electrodes of the pads when the pads are placed on skin areas above said anatomical points; and
   an input member for selecting one of a plurality of ensembles of points of therapy modalities/options.

2. The device according to claim 1, wherein at least one train of pulses of said trains of pulses comprises composite and modulated alternating bi-polar pulses; and further comprising a programming unit for composing said composite and modulated alternating bi-polar pulses.

3. The device according to claim 1, wherein said input unit includes an input member for varying an amplitude or frequency of said trains of pulses.

4. The device according to claim 1, wherein said input unit includes an input member for varying a modulation of said trains of pulses.

5. The device according to claim 1, wherein said input unit includes an input member for varying waveform shapes of said trains of pulses.

6. The device according to claim 1, further comprising:
a display for displaying said charts and health conditions.

7. The device according to claim 6, wherein the health conditions stored in the electronic memory are in a plurality of categories of health conditions, at least two health conditions in each category of the plurality of categories, and the electronic memory further stores information regarding each health condition of the plurality of health conditions.

8. The device according to claim 6, wherein said display and said input unit are integrated in a hand-held or palm-held unit.

9. The device according to claim 7, further comprising an input member for selecting one of the categories of health conditions, selecting a health condition within the selected category, and a chart identifying the anatomical points for treating the selected health condition.

10. The device according to claim 1, wherein the plurality of ensembles of points includes a first ensemble related to acupuncture points, a second ensemble related to trigger points, and a third ensemble related to Jin-Shin Jyutsu points.

11. The device according to claim 1 stimulates acupuncture points and obtains therapeutic effects of acupuncture treatment, without having to use acupuncture needles, and without having to puncture skin to reach acupuncture points as practiced in conventional acupuncture therapies.

12. The device according to claim 1 configured to stimulate muscles, tendons, ligaments, joints, and nerves to help restore and/or enhance functions, improve circulation, and reduce pain.

13. An electronic stimulating device comprising:
a memory for storing sequences of pulses for an ensemble of predetermined points on an anatomy;
an input unit for selecting a sequence of said pulses for a set of predetermined points from said ensemble of predetermined points;
a plurality of pads, each pad of the plurality of pads comprising an imbedded coil-shaped electrode configured to generate magnetic field in response to electrical current;
a pulse generator for generating the selected sequence of pulses and applying the pulses to the coil-shaped electrodes of the pads in proximity to said set of predetermined points;
wherein said input unit comprises an input member for providing user programmability of custom combinations of component pulse-trains to compose custom treatment pulse seciuences.

14. The device according to claim 13, wherein said input unit integrates data input and display functionality in a hand-held computing device.

15. The device according to claims 13, wherein:
said input unit further comprises an input member for varying a modulation of said pulses or waveform shapes of said pulses.

16. The device according to claims 13, wherein said input unit further comprises an input member for varying a frequency of said pulses or an amplitude of said pulses.

17. The device according to claims 12, further comprising:
a memory storing a plurality of electronically stored charts of said predetermined points, each chart being associated with a health condition; and
a display for displaying the charts and the associated health conditions.

18. The device according to claims 17, further comprising an electronic indexer for indexing each chart to the associated health condition, symptoms, and related condition.

19. The device according to claims 13, said input unit further comprising an electronic menu tree for selecting a respective one of a plurality of ensembles of acu-points.

20. The device according to claim 13, further comprising a display wherein said display and said input unit are separate.

21. An electronic stimulating device comprising:
a memory for storing sequences of pulses for an ensemble of predetermined points on an anatomy;
an input unit for selecting a sequence of said pulses for a set of predetermined points from said ensemble of predetermined points, said input unit comprising an electronic menu tree for selecting a respective one of a plurality of ensembles of acu-points;
a plurality of pads, each pad of the plurality of pads comprising an imbedded coil-shaped electrode configured to generate magnetic field in response to electrical current; and
a pulse generator for generating the selected sequence of pulses and applying the pulses to the coil-shaped electrodes of the pads in proximity to said set of predetermined points;
wherein the plurality of ensembles of acu-points includes a first ensemble related to acupuncture points, a second ensemble related to trigger points and a third ensemble related to Jin-Shin Jyutsu points.

22. An electronic stimulating device comprising:
an electronic memory storing a plurality of health conditions and a plurality of charts identifying anatomical points for treating the health conditions, the anatomical points being selected from a group consisting of acupuncture points, acupressure points, trigger points and Jin-Shin Jyutsu points;
an electronic indexer for indexing each health condition of the plurality of health conditions to a chart of the plurality of charts identifying the anatomical points for treating said each health condition;
an input unit for selecting trains of electrical pulses associated with the charts;
a plurality of pads, each pad of the plurality of pads comprising an imbedded coil-shaped electrode configured to generate magnetic field in response to electrical current; and
a pulse generator for generating the selected trains of electrical pulses and applying the selected trains of electrical pulses to the coil-shaped electrodes of the pads when the pads are placed on skin areas above said anatomical points;
wherein the device stimulates trigger points and obtains therapeutic effects of trigger point massage therapy, without having to use thumbs, knuckles, and elbows to apply pressure on trigger points as practiced in conventional trigger point massage therapies.

23. An electronic stimulating device comprising:
an electronic memory storing a plurality of health conditions and a plurality of charts identifying anatomical points for treating the health conditions, the anatomical points being selected from a group consisting of acupuncture points, acupressure points, trigger points and Jin-Shin Jyutsu points;

an electronic indexer for indexing each health condition of the plurality of health conditions to a chart of the plurality of charts identifying the anatomical points for treating said each health condition;

an input unit for selecting trains of electrical pulses associated with the charts;

a plurality of pads, each pad of the plurality of pads comprising an imbedded coil-shaped electrode configured to generate magnetic field in response to electrical current; and a pulse generator for generating the selected trains of electrical pulses and applying the selected trains of electrical pulses to the coil-shaped electrodes of the pads when the pads are placed on skin areas above said anatomical points;

wherein the device stimulates acupressure points and obtains therapeutic effects of acupressure, without having to use thumbs, knuckles, and elbows to apply pressure on acupressure points as practiced in conventional acupressure therapies.

24. An electronic stimulating device comprising:

an electronic memory storing a plurality of health conditions and a plurality of charts identifying anatomical points for treating the health conditions, the anatomical points being selected from a group consisting of acupuncture points, acupressure points, trigger points and Jin-Shin Jyutsu points;

an electronic indexer for indexing each health condition of the plurality of health conditions to a chart of the plurality of charts identifying the anatomical points for treating said each health condition;

an input unit for selecting trains of electrical pulses associated with the charts;

a plurality of pads, each pad of the plurality of pads comprising an imbedded coil-shaped electrode configured to generate magnetic field in response to electrical current; and a pulse generator for generating the selected trains of electrical pulses and applying the selected trains of electrical pulses to the coil-shaped electrodes of the pads when the pads are placed on skin areas above said anatomical points;

wherein the device stimulates Safety Energy Locks (SEL) as in Jin-Shin Jyutsu therapies, obtains the result without having to use hands and fingers to touch SEL for long durations as practiced in conventional Jin-Shin-Jyutsu therapies.

* * * * *

UNITED STATES PATENT AND TRADEMARK OFFICE
CERTIFICATE OF CORRECTION

PATENT NO. : 7,167,752 B2  
APPLICATION NO. : 10/439163  
DATED : January 23, 2007  
INVENTOR(S) : Catherine Lin-Hendel Page 1 of 1

It is certified that error appears in the above-identified patent and that said Letters Patent is hereby corrected as shown below:

Column 13, line 61, cancel the text beginning with "15. The device according to claims 13" and ending with "a plurality of ensembles of acu-points." in column 14, line 13; and insert the following claims:

--15. The device according to claim 13, wherein:
said input unit further comprises an input member for varying a modulation of said pulses or waveform shapes of said pulses.

16. The device according to claim 13, wherein said input unit further comprises an input member for varying a frequency of said pulses or an amplitude of said pulses.

17. The device according to claim 13, further comprising:
a memory storing a plurality of electronically stored charts of said predetermined points, each chart being associated with a health condition; and
a display for displaying the charts and the associated health conditions.

18. The device according to claim 17, further comprising an electronic indexer for indexing each chart to the associated health condition, symptoms, and related condition.

19. The device according to claim 13, said input unit further comprising an electronic menu tree for selecting a respective one of a plurality of ensembles of acu-points.--

Signed and Sealed this

Tenth Day of April, 2007

JON W. DUDAS  
*Director of the United States Patent and Trademark Office*